United States Patent [19]

Ainsworth et al.

[11] Patent Number: 5,696,153
[45] Date of Patent: Dec. 9, 1997

[54] THERAPEUTIC REGIMEN FOR TREATING PATIENTS

[75] Inventors: Sterling K. Ainsworth, Boulder, Colo.; Lawrence Helson, Chappaqua, N.Y.

[73] Assignee: NaPro BioTherapeutics, Inc., Boulder, Colo.

[21] Appl. No.: 685,155

[22] Filed: Jul. 23, 1996

Related U.S. Application Data

[63] Continuation of Ser. No. 243,595, May 16, 1994, abandoned.

[51] Int. Cl.$^6$ ............................................. A61K 31/335
[52] U.S. Cl. ............................................. 514/449
[58] Field of Search ..................................... 514/449

[56] References Cited

PUBLICATIONS

A Phase I Trial of Taxol Given by a 6–Hour Intravenous Infusion T. Brown, *Journal of Clinical Oncology*, vol. 9, No. 7 (Jul.) 1991; pp.1261–1267.

Annual Report to the Food and Drug Administration— Taxol, *Division of Cancer Treatment*, National Cancer Institute, Bethesda, Maryland, Feb. 1989.

Phase I Trial of Taxol in Patients with Advanced Cancer, R. Donehower et al, *Cancer Treatment Reports*, vol. 71, No. 12, Dec. 1987.

Phase I Study of Taxol Administered as a Short Iv Infusion Daily for 5 Days, J. Grem et al, *Cancer Treatment Reports*, vol. 71, No. 12, Dec. 1987.

Phase I Trial of Taxol Given as a 3–Hour Infusion every 21 Days, M. Kris et al. *Cencer Treatment Reports*, vol. 70, No. 5, May 1986.

Taxol Produces a Predominantly Sensory Neuropathy, R.B. Lipton et al, *Neurology*, 1989; 30:368–373.

High–Performance Liquid Chromatographic Assay for Taxol in Human Plasma and Urine and Pharmacokinetics in a Phase I Trial, S. Longnecker et al, *Cancer Treatment Reports*, vol.71, No. 1, Jan. 1987.

Taxol: An Important New Drug in the Management of Epithelial Ovarian Cancer, M. Markman, *The Yale Journal of Biology and Medicine, Inc.*, 64 (1991), 583–590.

Taxol: A new agent active in melanoma and ovarian cancer, A. Einzig et al., *New Drugs, Concepts and Results in Cancer Chemotheraphy*, vol. 58, 1991.

Taxol: Twenty Years Later, the Story Unfolds, E. Rowinsky et al, *Jourrnal of the National Cancer Institute*, vol.83, No. 24, Dec. 18, 1991.

Taxol: A Novel Investigational Antimicrotubule Agent, E. Rowinsky et al, *Review*, vol. 82, No. 15, Aug. 1, 1990.

Cardiac Disturbances During the Administration of Taxol, E. Rowinsky et al, *Journal of Clinical Oncology*, vol. 9, No. 9 (Sep. 1991) pp. 1692–1703.

New Natural Products in Cancer Chemotherapy, W.Slichenmyer et al., *Journal of Clinical Pharmacol*, 1990; 30:770–788.

Taxol: A new and Effective anti–cancer drug, W. Slichenyer et al., *Anti–Cancer Drugs*, vol. 2, 1991.

Hypersenitivity Reactions from Taxol, R. Weiss et al, *Journal of Clinical Oncology*, vol. 8, No. 7 (Jul. 1990) pp. 1263–1268.

Phase I Clinical and Pharmacokinetic Study of Taxol, P. Wiernik et al, *Cancer Research*, 47, 2486–2493, May 1, 1987.

*Primary Examiner*—Jerome D. Goldberg
*Attorney, Agent, or Firm*—Timothy J. Martin

[57] ABSTRACT

A method for administration of taxol by infusing taxol over a duration of 60 to 180 minutes for a pluratily of times during a 21 day period, each of said times being separated by an interval of between 4 to 5 days.

12 Claims, 1 Drawing Sheet

THERAPEUTIC REGIMEN FOR TREATING PATIENTS

This is a continuation of application Ser. No. 08/243,595 filed on May 16, 1994, now abandoned.

FIELD OF THE INVENTION

The present invention broadly concerns a treatment regimen in patients with various cancers. More specifically, the present invention relates to a therapeutic regimen (a treatment schedule) to administer the pharmaceutical compound known as taxol to patients having cancer in an effort to stabilize, reduce or destroy the cancerous growth. Specifically, the present invention concerns the duration of infusion, the timing and frequency of taxol infusion treatments and the dosage of taxol.

BACKGROUND OF THE INVENTION

Taxol is a natural product which has been shown to possess cytotoxic and antitumor activity. Indeed, taxol may be among the most active single agent for ovarian and breast cancers. This compound is found in small concentrations in the *Taxus brevifolia* species such as the Pacific yew tree among other Taxus species. While having an unambiguous reputation of tremendous therapeutic potential, taxol as a therapeutic agent has some patient related drawbacks. These stem, in part, from its extremely low solubility in water, which makes it difficult to provide in suitable dosage form. Because of taxol's poor aqueous solubility, the current approved clinical formulation consists of a 6 mg/ml solution of taxol in 50% polyoxyethylated castor oil (Cremophor El®) and 50% dehydrated alcohol. *Am. J. Hosp. Pharm.* 1991, 48:1520–24. In some instances, severe reactions occur in conjunction with the emulsifiers administered in conjunction with taxol to compensate for its low water solubility. As a result of the incidence of hypersensitivity reactions to taxol formulations and the drug's inherent toxicity, studies have been undertaken to determine more optimal infusion rates and dosing schedules for patients.

Early approaches to taxol administration were directed at short (1–3 hour) infusions, but the infusion of varying amounts of taxol has been associated with anaphylactic reactions and other hypersensitivity responses. Accordingly, patients were premedicated with a variety of reaction ameliorators and inhibitors, including steroids (such as dexamethasone), antihistamines (such as diphenhydramine), and $H_2$-antagonists (such as cimetidine or ranitidine). Moreover, in these early trials, the infusion time was extended to twenty-four hours or more in an attempt to delay or eliminate the most serious allergic reactions.

In Brown et al, "A Phase I Trial Taxol Given by a Six-Hour Interveneous Infusion", *J. Clin. Oncol.*, Vol. 9, No. 7, pp. 1261–1267 (July, 1991), a six-hour infusion of taxol was given every twenty-one days without premedication. The maximum tolerated dose reported was 275 mg/m$^2$, and the recommended phase II starting dose was 225 mg/m$^2$. The incidence of hypersensitivity reactions was reported to be dependent upon the schedule over which the taxol was administered.

Other protocols have been proposed for administering various dosages of taxol. For example, in Kris et al, *Cancer Treat. Rep.*, Vol. 70, No. 5 (May, 1986) a three hour infusion of taxol and Cremophor El® and dehydrated alcohol is described, and the dosage of taxol varied from 15 mg/m$^2$ to 200 mg/m$^2$. The conclusion reached in the study, however, was that this administration schedule was not recommended due to the severity and unpredictability of hypersensitivity reactions. In Koeller et al, "A Phase I Pharmacokinetics Study of Taxol Given by a Prolonged Infusion Without Premedication", *Proceedings of ASCO*, Vol. 8 (March, 1989) patients received dosages ranging from 175 mg/m$^2$ to 275 mg/m$^2$. A six hour IV infusion was tested using various different dosage levels as described in Wiernik et al, "Phase I Clinical and Pharmacokinetics Study of Taxol", *Cancer Research*, 47, 2486–93 (May, 1987). Here, the recommended Phase II trial dosages were recommended to be 250 mg/m$^2$ along with medication.

As a result of these and other studies, a continuous infusion of taxol over a twenty-four hour period on a twenty-one day schedule is often used. The same dose may be administered as a three hour infusion with equal effectiveness and less drug toxicity. Current approved recommended dosage is in the range of 135–175 mg/m$^2$ over an infusion time of 24 hours at a 21 day cycle, repeated three times (Q21d×3).

In response to the toxicity of taxol, hypersensitivity to its castor oil carrier and the increasing recognition of taxol's promise as an antineoplastic, there remains a need to develop improved protocols for the administration of this drug. Moreover, there is a need for techniques which can increase the effectiveness of the drug in reducing tumor growth.

SUMMARY OF THE INVENTION

It is an object of the present invention to provide a new and useful method for the administration of taxol.

It is a further object of the present invention to provide a method for the infusion of taxol over reduced durations so as to decrease patient care time and cost.

Yet another object of the present invention is to provide a method for providing dosage levels of taxol without negatively impacting its chemotherapeutic effect on cancer cells while at the same time decreasing toxicity and hypersensitivity reactions.

A still further object of the present invention is to provide a method for administering taxol by infusion that avoids hypersensitivity without premedication.

Still a further object of the present invention is to provide a method for infusing taxol as a chemotherapeutic agent in a manner that maximizes its cytotoxic activity against cancerous cells.

A further object of the present invention is to provide a method allowing an increase in the effective dosage of taxol given without increasing toxicity beyond acceptable limits.

To accomplish these objects, then, the general method according to the present invention is directed to the administration of taxol to a patient suffering from cancer. Broadly, the method comprises a therapeutic regimen of infusing an amount of taxol to the patient within a range of 45–120 mg/m$^2$ over a duration of 60–180 minutes for a plurality of times during a twenty-one day period with each of these plurality of times being separated from the next by an interval of between 4 to 5 days. Preferably, this protocol is repeated for three cycles of twenty-one days (63 days total) with the plurality of times of infusing the taxol beginning on the first day of each of the cycles. Preferably, the duration of each infusion is between about 60–80 minutes and there are three treatment days in each cycle separated by four non-treatment days. Moreover, it is preferred that the amount of taxol infused be about 60 mg/m$^2$.

These and other objects of the present invention will become more readily appreciated and understood from a consideration of the following detailed description of the exemplary embodiments when taken together with the accompanying drawings, in which:

DETAILED DESCRIPTION OF THE EXEMPLARY EMBODIMENTS

Figure 1:
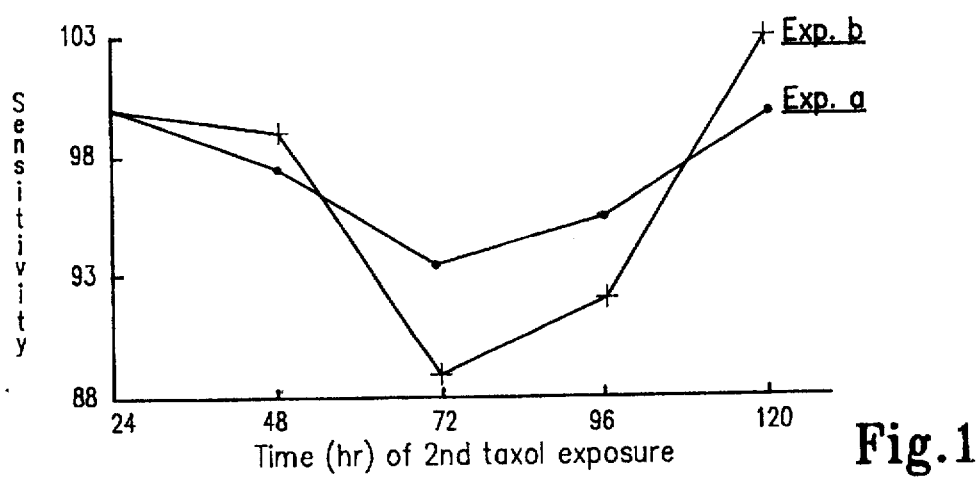
FIG. 1 is a graph showing the sensitivity of in vitro cancer calls (SK-N-AS) to a second dose of taxol at different times following a first dose thereof.

The present invention is directed to the administration of taxol to patients as a cancer treatment. As described more fully herein, this invention relates to the discovery that patients receiving between 45–120 mg/m$^2$ taxol with an infusion rate of 60–180 minutes on a Q4D×3 schedule exhibit less toxic reaction and side effects than equivalent dosage levels over a twenty-four hour infusion, with limited pretreatment. Moreover, based on in vitro and animal studies, indications are that the Q4D schedule increases the effectiveness of taxol treatment. While not quantified, this schedule has demonstrated effectiveness with human patients in limited tests conducted on salvage patients who had otherwise failed conventional therapy. The in vitro, animal and human studies will therefore be addressed in turn.

I. In Vitro Studies

Initial experiments were conducted to test the cytotoxic effects of taxol on in vitro cell cultures of cancerous cells. The target indicators measured were cell growth arrest, necrosis, apoptosis, polyploidy and cytophagia. Experimental design included: (1) determination of the dose/time/toxicity relationship following exposures to taxol of 15 minutes to 24 hours in cell lines; (2) determination of the lowest effective dose; and (3) the effect of brief multiple serial challenges with taxol, at intervals of hours to weeks.

A. Cell Lines

Cell lines tested included: Glioblastoma cell lines VA-MG-SL and U-373-MG, neuroblastoma cell lines SK-N-AS, SK-N-FI and VA-N-BR, and two primitive neuroectodermal tumor cell lines SK-N-LO and SK-PN-DW at different concentrations. All cell lines were personally established from patients and cultured except U-373-MG (obtained from the American Type Culture Collection, Rockville, Mich., USA). The cell lines SK-N-AS, SK-N-FI, SK-N-LO and SK-PN-DW have been reported in several publications and are believed to be representative of their respective lineages.

B. Taxol

Taxol, obtained as a 98.2% purified product (NaPro BioTherapeutics, Inc., Boulder, Colo.), was solubilized in 95% alcohol to 1000 µg/ml and further diluted with media to 0.1–20 µg/ml. Various concentrations of freshly diluted taxol were added to replicate wells in 0.1 ml volumes and removed after 1, 4 or 24 hours. In a separate experiment, we compared 0.3 µg/ml taxol added at 30 minute intervals twice versus 0.6 µg/ml; both lines were washed free of taxol after a total of 1 hour exposure.

C. Cytotoxicity Assays

The cytotoxic effects of taxol were determined in tumor cells growing as attached monolayers. Stock cells in 25 cm$^2$ flasks were incubated in Dubelco's modified Eagle's medium (Sigma, St. Louis, Mo.) containing 10% fetal bovine serum at 37° C. and 5% $CO_2$ in air for 5 days. Media was renewed on the sixth day and on the seventh day the cells were detached into a single cell suspension with trypsin EDTA, counted and aliquots plated at 3000 to 5000 cells in 0.1 ml fresh media in separate wells of a 96-well microliter plate (Becton-Dickinson Labware, Lincoln Park, N.J.). By 24 hours the cells formed attached monolayers. Six replicate wells were used in every experiment as controls and for each test concentration. Each experiment was repeated three separate times. Viability of the cell lines 5 days after exposure to drugs was determined by the MTT assay following published procedures.

To distinguish between taxol-induced growth inhibition and cytocidal activity, MTT readings and direct viable cell enumerations were compared at baseline and at 120 hours after drug exposure of control and treated cells. Cytocidal activity was defined when the number of cells or the MTT surrogate optical density value was less than the initial inoculum. This is usually the case when ≧80% toxicity is recorded under these in vitro conditions.

The significance of the differences between the mean values of control and treated cells on the fifth day after exposure to taxol were determined using Students t-test. Differences were considered to be statistically significant for a p-value of 0.05 or less.

D. Results

As is shown in Table 1, concentrations of 0.001 to 1.0 µg/ml taxol for 1–24 hours caused a range of graded responses which remained consistent over three separate experiments.

TABLE 1

| | Taxol Toxicity | | | |
|---|---|---|---|---|
| Cell line | Concentration | x 1 h | x 4 h | x 24 h |
| VA-MG-SL | 0.1 | 58 | 56 | 58[b] |
| | 1.0 | 87 | 90 | 86[b] |
| U-373-MG | 0.1 | 46 | 56 | 57[b] |
| | 1.0 | 74 | 79 | 79[b] |
| SK-N-AS | 0.01 | 15 | 25 | 50[a] |
| | 0.1 | 65 | 67 | 81[a] |
| | 1.0 | 87 | 82 | 89[b] |
| SK-N-FI | 0.1 | 0 | 0 | 14[a] |
| | 1.0 | 0 | 58 | 76[a] |
| VA-N-BR | 0.1 | 61 | 66 | 68[b] |
| | 1.0 | 87 | 84 | 83[b] |
| SK-N-LO | 0.01 | 0 | 0 | 17[a] |
| | 0.1 | 43 | 56 | 47[b] |
| | 1.0 | 54 | 58 | 57[b] |

[a]Significant differences (p < 0.05) comparing 1 and 24 hour incubation.
[b]Toxicity ≦80% was growth inhibition relative to untreated controls after 5 days incubation. When ≧80% cytotoxicity was recorded, it was cytocidal in nature.

All values presented are the means of sextuplicate wells compared to untreated controls 5 days after exposure to taxol. Concentrations of taxol, 0.01 µg/ml were toxic in SK-N-AS and SK-N-LO at ≧1 and 24 hour exposure, respectively. The remaining cell lines were affected only at concentrations ≧0.1 µg/ml.

SK-N-AS was the least resilient of the cell lines to taxol and SK-N-FI the most. The order of sensitivity to taxol exhibited by these cell lines remained consistent within the concentration range 0.01–1.0 µg/ml. The extent of toxicity following incubation for 1, 4 or 24 hour with 0.01, 0.1 and 1.0 µg/ml taxol was similar at each concentration for the two glioblastoma, and the VA-N-BR neuroblastoma cell line. At 0.01 µg/ml taxol for 24 hour the neuroblastoma SK-N-AS and the primitive neuroectodermal tumor cell line SK-N-LO exhibited enhanced cytotoxicity when compared with a 1 hour exposure. With reference to FIG. 1, cell cultures in two experiments "a" and "b" were subjected to a first dose of taxol and then dosed a second time varying from 24 to 120 hours later. Sensitivity (the ordinate axis) was measured. it may be seen that the sensitivity rebounded at the fourth day and continued to the fifth day to the original sensitivity levels.

After exposure of SK-N-AS to 1 µg/ml taxol for 1 hour, cytopathologic changes were characterized by apoptosis at 6–24 hours, abnormal mitosis and polyploidy at 36–72 hours, and death of cells between 72 and 144 hours. Approximately 30% of the cells appeared to be altered by taxol at any of the time points (24, 48 and 72 hours) of observations. Apoptosis was recognized as acute change in the cells. These included chromatin clumping at the periphery of the nucleus, loss of cytoplasmic detail and finally apoptotic bodies, either readily detached or floating with several being phagocytosed by surrounding cells.

The cytotoxic effects of a single exposure to taxol at 0.6 µg/ml/h in SK-N-AS were greater than when taxol was scheduled as 0.3 µg/ml given once and once again after 30 minutes, as shown in the following Table 2:

TABLE 2

Effects of Spacing Exposure to Taxol
On Toxicity in Sk-N-AS Cells

| Concentration | Survival (%) |
| --- | --- |
| 0.6 µg/ml for 60 minutes | 24 + 4 |
| 0.3 µg/ml for 30 minutes × 2 | 61 + 6 |

Since determination of the growth rates of untreated and treated cells is dependent upon the size of their initial inocula and the degree of confluency in each well during the time of treatment, all inocula and incubation times were standardized in order to minimize these variables. We also compared trypan blue viable cell enumeration daily with MTT values in replicate wells and found them to be sufficiently consistent to use either technique.

The similarity in quantitative cytopathic effects following taxol exposures of 1, 4 or 24 hours at concentrations within the range 0.01–1.0 µg/ml in three cell lines suggested that an upper limit of drug cytotoxic effect exists. When reached within a short time frame, this precludes additional drug-induced effects, suggesting for taxol, the notion of a saturable microtubule target.

In using the MTT assay we identified a discrete subpopulation of surviving tumor cells which obviously exhibit lesser sensitivity to taxol than the cells which died. This lack of homogeneity in taxol sensitivity of serially cultured tumor cells reflects differences in replicative activity as well as cytotoxic susceptibility and could explain why the 0.6 µg/ml impacts upon a broader cohort of the "taxol susceptible" cells than 0.3 µg/ml.

Presumably saturation of microtubule taxol receptors defines an upper limit of cytotoxic activity while leaving a residue of unbound microtubules. Disruption of unbound microtubules may follow either additional exposure to taxol at appropriate intervals or other drugs with different mechanisms of action. Based upon a three to four cell cycle generation time frame, occurrence of apoptosis at 24 and 96 hours after exposure, and duration of retained intracellular taxol (>8 days), we concluded revertant taxol susceptibility may occur as early as four days after initial exposure. Thus, fractionated dosage should follow a preceding dosage 4 to 5 days later to allow for the return of sensitivity.

These results in cell culture experiments therefore imply that an infusion of 175 mg/m$^2$ taxol in a 24 hour period might not be the most effective protocol. If, in patients, serum taxol levels following 175 mg/m$^2$/24 hours exceed threshold levels required to induce maximum cytotoxic effects, the efficiency of the currently approved dosage strategy may be limited. A greater benefit would therefore be derived from a more efficient schedule which would avoid the maximally tolerated dosages of taxol at any single setting yet which would still provide equal or greater does intensity schedules than those described in current labelling. An infusion protocol for humans based on an 80 minute infusion of taxol at 60 mg/m$^2$ every 4 days×3 was therefore justified. This would fractionate the infusion dosage to about one-third the maximum recommended dosage (175 mg/m$^2$) or to about one-half the typical dosage (135 mg/m$^2$). This also indicates that dosage as low as 45 mg/m$^2$ or as high as 120–135 mg/m$^2$ might be appropriate per infusion. To accord with dose intensity schedules of 525 mg/m$^2$ every 63 days currently recommended, a repetition of three courses of about 60 mg/m$^2$ would yield the same overall administered quantity.

II. Animal Studies

We next determined taxol distribution in tissues of tumored nude mice following: (A) a single intraperitoneal (IP) injection ("Study A"); (B) three IP injections at 4 day intervals ("Study B"); (C) 24 hours after a single pulse injection 5 days following a series of three IP injections at 4 day intervals ("Study C"). For antitumor activity we measured mouse weight and tumor size; for subjects in Studies B and C, we measured mouse weight prior to the single pulse injection, and in an additional Study D after three IP injections of taxol at 4 hour intervals during 24 hours.

A. Materials Taxol was obtained from NaPro BioTherapeutics, Inc., 2885 Wilderness Place, Suite B, Boulder, Colo. 80301, as a 99.2% purified product. It was formulated in Cremophor El® according to the descriptions previously referred to and as is well known in this art. Five nude mice were maintained in each cage with a fiberglass bonnet in a clean isolation room. All cages and food were sterilized prior to use. Female nude mice were inoculated subcutaneously with 3×10$^6$ human neuroblastoma (SK-N-AS) tumor cells. Between 8–16 days, tumor growth was evident and measured.

B. Methods

For Study A, freshly prepared taxol: 40 mg/kg in 0.5 ml alcohol and Cremaphor El®, was injected intraperitoneally. Individual mice were sacrificed on days 1–6 post-taxol inoculation and the concentration of taxol in tumor and organs was determined. Following sacrifice by cervical dislocation, tumor and normal tissues were immediately removed, sonicated, diluted in buffer (PBS containing 0.25% BSA, 0.05%, Tween 20, Methanol 20%, and Sodium Azide 2%). The concentration of taxol in tissue was assayed using an enzyme-linked immunoassay kit (Hawaii BioTechnology Group, Inc., 99–193 Aiea Heights Drive, Liea, Hi. 96701). Tissue protein was determined using the BioRad kit (BioRad, 3300 Regatta Boulevard, Richmond, Calif. 94804).

To determine tissue accumulation of taxol after repeated dosing, in Study B we measured taxol levels in a group of tumored nude mice previously injected with 15 mg/kg taxol once every 4 days×3 on the sixth and seventh days following the last dose. In Study C, mice were treated three times with taxol at 10 mg/kg IP at 4 day intervals and then after 9 days observation were injected IP once with taxol at 20 mg/kg. Twenty-four hours later, these mice were sacrificed and taxol tissue levels in tumors and organs were determined and compared with levels observed in control tumor induced mice injected with 20 mg/kg taxol IP only once the previous day.

To determine antitumor activity, 15 mg/kg taxol IP injected every 4 days for three doses (Study B) was compared with 15 mg/kg every 4 hours in a single day for 3 doses (Study D). In Study C, taxol injections at 10 mg/kg IP dose Q4D×3 were started when tumors were well established and weights and tumor sizes were recorded after 9 days observation.

C. Results

The purpose of these studies was to determine the distribution of taxol in tissues and any concomitant antitumor activity. In Study A, based on a ng/mg tissue protein basis, taxol was detected in tumor, lung, kidney, liver, spleen and heart 24 hours post-injection. In 48 hours all tissues except the tumor contained less than 10 ng/mg protein. At 72 hours taxol remaining in tumor, heart and spleen tissue was in very reduced concentrations, as is shown in the following Table 3:

TABLE 3

Taxol Levels* in Mice Organs: Days After Single IP Injections

| Day | 1 | 2 | 3 | 4 | 5 | 6 |
|---|---|---|---|---|---|---|
| Dose mg/kg | 40 | 40 | 40 | 40 | 40 | 40 |
| Tumor | 93.3 | 38.0 | 0.27 | 0.22 | 0.55 | 0.23 |
| Size mm² | 378 | 480 | 208 | 80 | 252 | 154 |
| Heart | <10 | <10 | 1.7 | ND | ND | ND |
| Liver | 30.36 | <10 | ND | ND | ND | ND |
| Spleen | 11.07 | <10 | ND | ND | ND | ND |
| Kidney | 7.23 | <10 | ND | ND | ND | ND |
| Lung | 28.0 | <10 | ND | ND | ND | ND |

Values designated <10 were samples diluted 1:10 without taxol being detected. These same samples undiluted contained <9.9 ng/mg protein - (0.22–9.9 ng/ml).
ND—NOT DETECTED
*ng taxol/mg protein In Study B, the Q4D schedule of taxol, there were no indications of toxicity as defined by wasting or weight loss. Taxol was detectable in tumor and organs seven days after the third injection. Substantial amounts were noted in the colon. In Study C, after challenge with a single injection of 20 mg/kg IP the concentration in normal tissues in treated mice was consistently greater than in nontreated controls and the concentration of taxol was usually greater in tumor tissue compared to liver, kidney or lung. The following Tables 4 and 5 summarize these results:

TABLE 4

Taxol ng/mg Protein in Nude Mice^A

| Mouse | | D14/D1 Area | Kidney | Spleen | Lung | Liver | Tumor |
|---|---|---|---|---|---|---|---|
| Controls | NT | 9.47 | 0.69 | 3.1 | 5.16 | 0.47 | 6.5 |
| Cage I | CT | 9.17 | 0 | 1.1 | 2.08 | 3.63 | 92.68 |
| | CLE | 5.45 | 14.23 | 6.92 | 0.39 | 4.8 | 103.57 |
| Created | NT | 5.4 | 0 | 10.91 | 16.67 | 4.32 | 195.24 |
| Cage II | CT | 0.74 | 0 | 5.85 | 25.67 | 5.47 | 7.0 |
| | CLE | 2.65 | 61.76 | 15.0 | 34.44 | 26.0 | 79.55 |
| Cage III | NT | 1.35 | 23.33 | 10.5 | 28.09 | 23.68 | 106.45 |
| | CRE | 1.35 | 60.53 | 119.05 | 23.26 | 28.0 | 12.9 |

^A All mice injected with 20 mg/kg IP 24 hours prior to assay
D14/D1 = Change in tumor area Day 14 compared with Day 1

TABLE 5

Cytotoxic Effects of Taxol in Nude Mice Bearing SK-N-AS Tumor

| | | Day #1 | | Day #5 | Day #9 | Day #14 | |
|---|---|---|---|---|---|---|---|
| | | Area | Wt | Area | Area | Area | Wt |
| Controls | NT | 38.5 | 29.7 | 132 | 285 | 360 | 33.8 |
| Cage I | CT | 36 | 27.2 | 100 | 232 | 330 | 33.3 |
| | CLE | 33.7 | 31.2 | 77 | 85 | 180 | 34.1 |
| | CRE | 67.5 | 29.7 | 126 | 207 | 250 | 32.8 |
| | MEAN | 43.9 | 29.5 | 108.9 | 202 | 280 | 33.5 |
| | S.E. | ±8.9 | ±0.8 | ±12.7 | ±42 | ±40.6 | ±0.29 |
| Treated | NT | 63 | 25.7 | 178 | 195 | 340 | 30.8 |
| Cage II | CT | 65 | 23.5 | 60 | 58 | 48 | 25 |
| | CLE | 68.5 | 28.5 | 78 | 91 | 180 | 29.6 |
| Treated | NT | 65 | 29.2 | 77 | 104 | 88 | 30.6 |
| Cage III | CRE | 40 | 25.9 | 72 | 80 | 54 | 27.8 |
| | MEAN | 60.3 | 26.6 | 93 | 105.6 | 142 | 28.8 |
| | S.E. | ±5.1 | ±1 | ±21.5 | ±23.6 | ±54.8 | ±1.1 |

Figure 2:
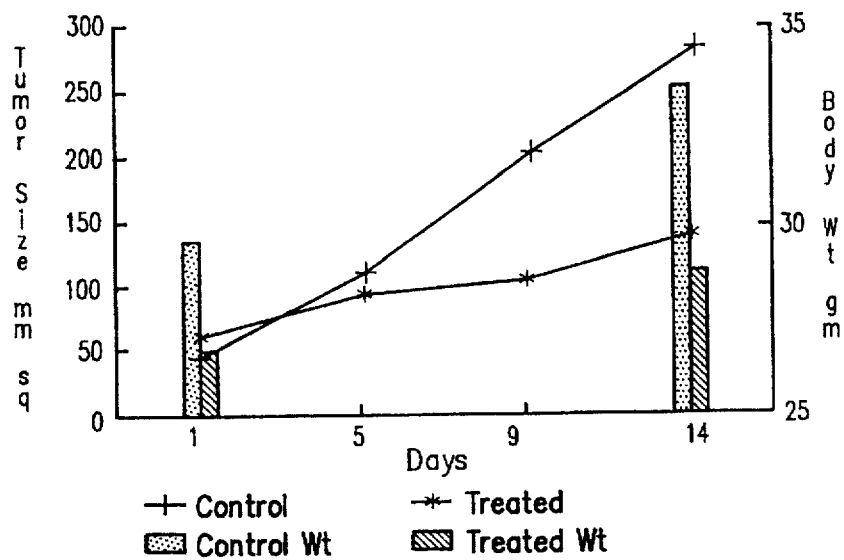
FIG. 2 is a graph of neuroblastoma (SK-N-AS) in nude mice in response to intraperitoneal injection of taxol (10 mg/Kg; Q4D×3) in the animal studies described herein.
Figure 3:
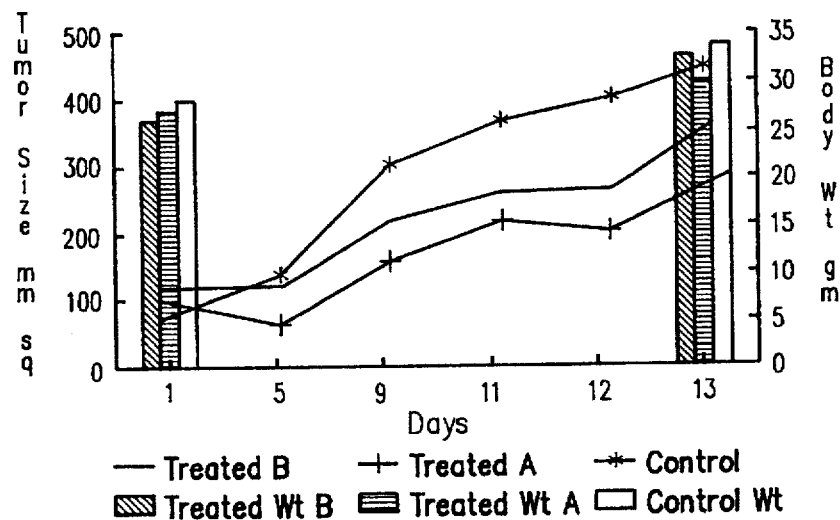
FIG. 3 is a graph of neuroblastoma (SK-N-AS) in nude mice in response to intraperitoneal injection of taxol (Q4D×3 vs. Q4H×3) in the animal studies described herein.

The data from Studies B and D suggest that the Q4D×3 schedule has greater antitumor activity than the Q4H×3 schedule, as shown in FIG. 1. In Study C, treatment with taxol consistently delayed tumor growth in 4/5 mice and caused tumor regression in 1/5 mice as is shown in Tables 4 and 5 and as is graphed in FIG. 2. The most responsive tumors were white and fibrotic on gross section. The response varied from tumor cell lysis to slowed growth. The small number of animals per group limited statistical comparisons to toxicity evaluations. In treated mice there was no significant weight gain between day 1 and day 14, while in untreated control mice there was a significant increase in weight and tumor size.

Since the design of this experiment was to determine the distribution, toxicity and any evidence of antitumor activity of three injections of taxol at only a moderate dosage (10 mg/kg), curability or efficacy was not a goal. We observed: (1) the distribution of taxol was four to thirty times greater in tumor tissue compared to liver, kidney or lung based on a ng/mg tissue protein basis; (2) the concentration in normal tissues in Group B mice as consistently greater than in Group A, when challenged with a single injection of 20 mg/kg IP; (3) a wide variance in response to drug therapy ranging from tumor lysis to slowed growth occurred; (4) overall, in Treated Group B there was no significant difference in tumor sizes or weight gain between day 1 and day 14, while in Control Group A mice there was a significant increase in both tumor size and weight.

Reasons for the apparent preferential taxol accumulation in tumor may be impeded clearance due to stagnant circulation, decreased metabolism, or enhanced binding in the heterotransplant. The relatively high concentration of taxol observed in the colon remains unexplained. It could be due to proportions of the unique muscle nerve and fat or irreversible intracellular binding. Drugs like taxol are secreted by the liver into the bile and are passed into the intestines, and reabsorbed in the small intestines. However, this enterohepatic recirculation would not explain the colonic distribution.

From these animal studies, the following was surmised: (1) taxol at 10 mg/kg IP Q4D×3 is a non-toxic dosage for neuroblastoma tumor bearing nude mice; (2) this dosage, while not the maximally tolerated dosage for mice, causes antitumor activity ranging from tumor growth inhibition to tumor lysis; (3) the distribution of taxol is favored in tumor tissue over normal tissue both acutely (24 hours after IP injection) and, even more so, chronically after three IP injections; (4) repetitive dosing impacts upon tissue taxol levels and may tend to exaggerate accumulation, i.e., alter clearance; (5) antitumor activity was better in the Q4D than in the QD schedule; and (6) identical treatment with taxol as 15 mg/kg every 4 days×3 or every 4 hours×3 in one day, was equally non-toxic.

It is known that the mouse has a surface area to weight ratio that is a factor of about ten times that of human. Thus, a mouse dosage of taxol at a level of 10 mg/kg suggests a human dosage of 1 mg/kg. For a 70 kg human having a 1.7m$^2$ surface area this translates into 70 mg dosage. Accordingly, a 10 mg/kg mouse dosage equals a 40 mg/m$^2$ dosage for humans. These animal studies at 15 mg/kg therefore indicate an optimal human dosage of about 60 mg/m$^2$ or 55 greater.

III. Human Studies

From the results obtained from the in vitro and the animal studies, responses of various human subjects to the Q4d×3 (21 days×3) protocol at dosages levels of about 60 mg/m$^2$ were evaluated. It should be understood that these patients were deemed "salvage" cases almost all of whom had not responded to conventional treatment. All were otherwise thought to be beyond approved therapeutic regimens. Thus, the results and evaluation are anecdotal in nature and are not part of a controlled and statistical valid clinical trial.

A. Study X

Twenty-three patients received 1–3 courses of taxol; of these twenty were evaluated for toxicity and responses. Characteristics of the group of twenty were: male (5); female (15); median age 44 (17–81); ECOG-PS 1 (0–3). All were previously treated with chemotherapy and radiation for cancers of the breast (5), ovarian (2), brain (3), prostate (1), head and neck (4), bone (2), leiomyosarcoma (2), and melanoma (1).

Assays of serum taxol concentrations from 105 treatments of 60 mg/m$^2$ over 80 minutes in the 23 patients using an ELISA method with NaPro BioTherapeutics, Inc., taxol standards revealed on 80th-minute median $C_{MAX}$ of 1000 ng/ml (range 100–3400); distributive phase $T_{1/2}\alpha$ was 7–20 minutes, and 0–40 ng/ml $C_{MAX}$ suggested levels <500 and >1500 ng/ml could be low and high cut-off points for stratifying patients for analysis of toxicity or response. In one patient with Ommaya reservoir placed as part of his glioblastoma management, we found intraventricular taxol concentrations to be 1% of his peripheral blood $C_{MAX}$ (1240 and 1400 ng/ml) during the course of two separate treatments. Neither sinus bradycardia, myalgia, neutropenic fever, clinically significant serum biochemical abnormalities, or infection were observed.

In the patient population in 115 treatments, grade II hypersensitivity reactions (2), stomatitis (1), and grade II neutropenia in 6 patients lasting 2–3 days were noted. Four patients exhibited malaise and fatigue immediately after the first 2 or 3 treatments. Alopecia occurred in 2/4 measurable patients, after 6–8 treatments. One patient with disseminated breast cancer had diploplia for several hours each day following treatment. After a single 60 mg/m$^2$ dose, one osteogenic sarcoma patient recovering from high-dose methotrexate hepatotoxicity developed pedal dysaesthesia lasting >3 weeks. This patient's $C_{MAX}$ was 1200 ng/ml, and $T_{1/2}\alpha$ 15 minute.

Toxicity was evaluated for these patients based on 172 evaluable treatments, and the results are summarized in Tables 6 and 7.

TABLE 6

Toxicity on CBC & SMAC Q4D Schedule at 60 mg/m$^2$

|  | A None | B Abnormal pre-III Improved | C Abnormal pre-III Worsened or same | D Normal pre-III Worsened | E Grades |
|---|---|---|---|---|---|
| HB | 18 | 1 | 2 | 2 | 1,4 |
| WBC | 15 | 0 | 2 | 6 | 1,1,2,3,3,4 |
| PLT. | 19 | 0 | 3 | 1 | 3 |
| Bilirubin | 22 | 0 | 0 | 1 | 1 |
| SGOT | 20 | 0 | 0 | 3 | 1,1,1 |
| GGT (11 pts) | 9 | 2 | 0 | 0 |  |
| Alk. Phos. | 18 | 3 | 1 | 1 | 1 |
| T P (22 pts) | 21 | 0 | 0 | 0 |  |
| Alb. (22 pts) | 22 | 0 | 0 | 0 |  |
| LDH (22 pts) | 18 | 3 | 0 | 0 |  |
| BUN (22 pts) | 21 | 0 | 0 | 0 |  |
| Creat (22 pts) | 21 | 0 | 0 | 0 |  |

No abnormalities detected on UA., CA$^{++}$, Phos, CO2, Cl, Na$^+$, K$^+$, Mg$^+$.

TABLE 7

Q4H 60 mg/m$^2$ Taxol
Patient Episodes and Grades of Toxicity

| Grade | 2 | 3 | 4 | 5 |
|---|---|---|---|---|
| Nausea | 1 |  |  |  |
| Vomiting | 1 | 4 |  |  |
| Stomatitis | 1 |  |  |  |
| Diarrhea | 4 |  |  |  |
| Constipation | 2 |  |  |  |
| Anorexia | 1 |  |  |  |
| Taste | 1 |  |  |  |
| Paresthesias | 1 |  |  |  |
| Arthralgia | 1 |  |  |  |
| Skin Rash | 1 |  |  |  |
| Hypersensitive | 1 | 2 |  |  |
| Alopecia | 4 |  | 4 |  |
| Fatigue | 1 |  | 2 |  |

B. Study Y

A pilot study of children with recurrent or refractory cancer was initiated under our direction. Ten patients with a variety of recurrent or refractory solid tumors of childhood were treated with the same dosage and schedule as the adults described above. One patient with a recurrent post-irradiation/chemotherapy resistant glioblastoma multiforme had a documented 30% decrease in tumor volume after 9 treatments. A second patient with post-irradiation and chemotherapy-resistant pelvic embryonal rhabdomyosarcoma had shrinkage of his tumor, demonstrated on CT scan.

However, he developed a brain metastasis shortly following the 9th treatment. These data suggest that there may be a distinction between taxol sensitivity of CNS primary tumors and metastatic cancer.

C. Conclusion

Our current interpretation of these data indicate that this schedule has no clinically significant $C_{MAX}$ taxol-associated toxicity and has antitumor activity in advanced disease patients with varied histologies. This Q4D dosage schedule in previously untreated patients or in combination/sequence with other active drugs or radiation appears to be equal to, or more effective than, the Q21 day schedule. However, in that these are Phase I studies on salvage patients radomized clinical trial comparing the Q4D versus the Q10 regimens has not been done.

Moreover, while the two human studies provide only anecdotal information, the fact that a complete response was shown in one case (brain tumor) and a partial response was observed in four instances (breast (2), head and neck (1), and brain (1)), in previously unresponsive patients or other patients who were deemed only to be candidates for salvage treatments suggests that treatment according to the Q4D×3 regimen has viability. The results of the toxicity analysis moreover indicate that the same or greater dosages as those currently recommended may be administered with the Q4D treatment regimen with reduced toxicity or hypersensitivity reactions. This was the case even where no pretreatment was administered prior to the infusion of taxol over a shorter duration.

Generalization of Method

According to the method of the present invention therefore, a method for administration of taxol is provided for patients suffering from cancer. This method comprises a protocol of infusing an amount of taxol within a range of 45–120 mg/m$^2$ over a duration of 60–180 minutes a plurality of times during a twenty-one day period with each of these times being separated by an integral of 4–5 days. Where 45 mg/m$^2$ of taxol is administered, three times during the twenty-one day cycle, such corresponds to an amount equal to the currently employed dosage of 135 mg/m$^2$ over a twenty-four hour infusion duration each twenty-one days. The amount of 120 mg/m$^2$ corresponds to the maximum amount found to be infused over an 80 minute interval without exceeding toxicity limits.

While as little as 60 minutes and as great as 180 minutes for the infusion duration was used, the preferred infusion time was about 60–80 minutes, and the amount of taxol infused was preferred to be 60 mg/m$^2$. This later amount of taxol corresponds to the maximum recommended dosage of 175 mg/m$^2$ in any twenty-one day cycle. Moreover, it was found that, by separating the treatment days by 3–5 days, but preferably 4 days, the toxicity of the taxol infusion was diminished.

Accordingly, the generalized method according to the present invention employs three twenty-one day cycles wherein 60 mg/m$^2$ is infused over a 60–80 minute duration on the 1st, 5th and 9th day of each twenty-one day cycle. The total amount of taxol thus administered over a 63 day period is slightly greater than the 525 mg/m$^2$ currently approved by the United States Food and Drug Administration, yet these infusions are accomplished with reduced toxicity. Further, this treatment regimen provides cost savings since the patient care time is reduced from the typical twenty-four hour infusion since the fractionalized infusions total 3–4 hours.

Accordingly, the present invention has been described with some degree of particularity directed to the preferred embodiment of the present invention. It should be appreciated, though, that the present invention is defined by the following claims construed in light of the prior art so that modifications or changes may be made to the preferred embodiment of the present invention without departing from the inventive concepts contained herein.

We claim:

1. A method for administration of taxol to a patient suffering from cancer which is sensitive to treatment with taxol comprising a protocol of infusing an amount of taxol within a range of 45 to 120 mg/m$^2$ over a duration of 60 to 180 minutes a plurality of times during a 21 day period, each of said times being separated by an interval of between 4 to 5 days.

2. A method according to claim 1 wherein the amount of taxol infused is within a range of 60 to 120 mg/m$^2$.

3. A method according to claim 1 wherein the amount of taxol infused is about 60 mg/m$^2$.

4. A method according to claim 1 wherein the duration is between about 60 to 80 minutes.

5. A method according to claim 1 wherein the taxol is infused three times during the 21 day period.

6. A method according to claim 5 wherein the interval between the times of infusion is about four days.

7. A method according to claim 1 wherein the interval between the times of infusion is about four days.

8. A method according to claim 1 including the step of repeating said protocol for three cycles with the plurality of times for each said cycle beginning on a first day thereof.

9. A method for administration of taxol to a patient suffering from cancer which is sensitive to treatment with taxol comprising a protocol of infusing a dosage of taxol on each of three treatment days in a twenty-one day cycle beginning on a first day thereof and wherein each of the treatments in the cycle is separated by between 4–5 non-treatment days and wherein said dosage of taxol is in an amount of between 60–120 mg/m$^2$ infused over a duration of 60–180 minutes.

10. A method according to claim 9 including the step of administering said taxol for three of said cycles.

11. A method according to claim 9 wherein the dosage of taxol is about 60 mg/m$^2$ infused over a duration of between 60–80 minutes on each treatment day.

12. A method for administration of taxol to a patient suffering from cancer comprising the infusion on a treatment day of about 60 mg/m$^2$ taxol over a period of about 60–80 minutes, there being three such treatment days separated in time by between 3–5 non-treatment days.

* * * * *